United States Patent
Sievert et al.

(10) Patent No.: US 6,229,058 B1
(45) Date of Patent: *May 8, 2001

(54) PREPARATION OF FLUORINATED PROPANES AND PENTANES

(75) Inventors: Allen Capron Sievert, Elkton, MD (US); Mario Joseph Nappa, Newark, DE (US)

(73) Assignee: E. I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/919,757

(22) Filed: Aug. 28, 1997

Related U.S. Application Data

(63) Continuation of application No. 08/660,509, filed on Jun. 7, 1996, now abandoned, which is a continuation of application No. 08/438,000, filed on May 10, 1995, now abandoned, which is a division of application No. 08/166,431, filed on Dec. 14, 1993, now Pat. No. 5,488,189.

(51) Int. Cl.$^7$ .................................................. C07C 19/08
(52) U.S. Cl. ........................... 570/134; 570/135; 570/137
(58) Field of Search .................... 570/134, 137, 570/135

(56) References Cited

U.S. PATENT DOCUMENTS

| | | | |
|---|---|---|---|
| 2,462,402 | 2/1949 | Joyce, Jr. ............................. | 260/653 |
| 3,377,393 | * 4/1968 | Yale ....................................... | 570/137 |
| 4,359,371 | * 11/1982 | Bohm .................................... | 570/137 |
| 4,801,763 | * 1/1989 | Maul ..................................... | 570/137 |
| 5,017,718 | * 5/1991 | Ojima et al. ......................... | 570/137 |
| 5,157,171 | 10/1992 | Sievert et al. ........................ | 570/151 |
| 5,177,274 | 1/1993 | Aoyama et al. ..................... | 570/172 |
| 5,326,913 | * 7/1994 | Aoyama et al. . | |

FOREIGN PATENT DOCUMENTS

| | | | |
|---|---|---|---|
| 2070924 | * 12/1997 | (CA) . | |
| 0 518 353 | 12/1992 | (EP) . | |
| 0078925 | * 5/1985 | (JP) ..................................... | 570/137 |
| 4-193841 | 7/1992 | (JP) . | |
| 4-253928 | 9/1992 | (JP) . | |
| 4-305542 | 10/1992 | (JP) . | |
| 5155789 | 6/1993 | (JP) . | |
| 525300 | 6/1979 | (SU) . | |
| WO 93/09081 | 5/1993 | (WO) . | |
| WO 93/16973 | 9/1993 | (WO) . | |

OTHER PUBLICATIONS

Lovelace et al Aliphatic Fluorine Compounds pp. 57, 71, 1958.*

Donald D. Coffman, Richard Cramer and G. W. Rigby, Synthesis of Chlorofluoropropanes, 71, 979–980, Mar., 1949.

P. Tarrant, et al., Ionic Addition Reactions of Halomethanes with Fluoroolefins, 8, 39–71, 1977.

\* cited by examiner

*Primary Examiner*—Alan Siegel
(74) *Attorney, Agent, or Firm*—James E. Shipley

(57) ABSTRACT

The instant invention relates to producing fluorinated propanes and pentanes. More particularly it relates to producing perhalofluoropropanes and pentanes by reacting dihalodifluoromethanes with polyfluoroethylenes, notably tetrafluoroethylene (TFE) and chlorotrifluoroethylene (CTFE) while in the presence of an aluminum chlorofluoride catalyst.

8 Claims, No Drawings

PREPARATION OF FLUORINATED PROPANES AND PENTANES

This is a continuation of application under 37 CFR 1.62 of prior application Ser. No. 08/660,509 filed Jun. 7 1996 now abandoned, which is a continuation of Ser. No. 08/438,000 filed on May. 10, 1995, now abandoned which is a division of Ser. No. 08/166,431 filed Dec. 14, 1993 now U.S. Pat. No. 5,488,189.

FIELD OF THE INVENTION

The instant invention relates to producing fluorinated propanes and pentanes. More particularly it relates to producing perhalofluoropropanes and pentanes by reacting dihalodifluoromethanes with polyfluoroethylenes, notably tetrafluoroethylene (TFE) and chlorotrifluoroethylene (CFFE) while in the presence of an aluminum chlorofluoride catalyst.

In another aspect, the instant invention relates to preparing novel perbromofluoroalkanes containing three, or five carbon atoms.

In still another aspect, the instant invention relates to a process for converting the perhalofluorocarbons to hydrofluorocarbons(HFCs) by reaction with a source of active hydrogen effective to convert one or more carbon-nonfluorohalogen bonds to carbon-hydrogen bonds.

Thus, the perhalofluoropropanes and pentanes, products of the inventive process, are potentially useful for manufacturing hydrofluorocarbons which, in turn, in view of their inherently low ozone depletion potentials, are environmentally attractive alternatives for perchlorofluorocarbons (CFC's) in such established uses as refrigerants, expansion agents, aerosol, propellants, fire extinguishing agents, power cycle working fluids, polymerization media, heat transfer media, solvents, carrier fluids, cleaning and drying agents, gaseous dielectrics, among other applications.

BACKGROUND OF THE INVENTION

Joyce, U.S. Pat. No. 2,462,402 (Feb. 22, 1949) discloses a process for the production of highly halogenated fluoro-alkanes which comprises contacting TFE with a polyhalo-genated alkane,preferably a methane, containing at least one chlorine atom and no more than two fluorine atoms, in the presence of a polyvalent metal halide catalyst, preferably aluminum chloride.

U.S. Pat. No. 2,462,402, to Coffman, et. al., is referenced in the Journal of the American Chemical Society, Vol. 71, pages 979–980 (1949) which discloses that reacting CHClF2 (chlorodifluoromethane) while in the presence of aluminum chloride with TFE produces CHCl2F5 having one less F atom than the sum of fluorine atoms in the reactants. Likewise, CHClF2 reacting with CTFE yields CHCl3F4.

Paleta, in a review article "Fluorine Chemistry Reviews", Vol. 8, page 51 (1977) states: "The ionic addition reactions of fluoromethanes in the presence of aluminum chloride are limited to the monofluoro derivatives only. When in contact with aluminum chloride, both difluorodichloromethane and difluorochloromethane were found to undergo a rapid disproportionation with the formation of monofluorochloromethanes (along with some further compounds) that are able to add to fluoroethylenes."

The disclosure of each of the previously identified references is hereby incorporated by reference.

SUMMARY OF THE INVENTION

One aspect of this invention relates to a process for producing valuable perhalopolyfluoropropanes and pentanes from known dihalodifluoromethanes, particularly dichlorodifluoromethane, and polyfluoroethylenes, such as tetrafluoroethylene (hereinafter referred to as "TFE") and chlorotrifluoroethylene (hereinafter referred to as "CTFE").

Another aspect of the invention provides such a process that produces propanes and pentanes wherein the total number of fluorine atoms is equal to the sum of the number of fluorine atoms in the dihalodffluoromethane reactant and the number of fluorine atoms in the polyfluoroethylene reactant.

Still another aspect of the invention relates to novel perbromofluoropropanes and pentanes.

A still further aspect of the invention relates to a process for obtaining hydropolyfluoropropanes and pentanes having relatively low ozone depletion potentials wherein carbon-nonfluorohalogen bonds, e.g., C—Cl or C—Br bonds, of the perhalofluoropropanes and pentanes are converted to carbon-hydrogen bonds.

Notwithstanding conventional beliefs as described in Paleta, the instant invention can react dihalodifluoromethanes, wherein the halo corresponds to non-fluoro halogens, with TFE and/or CTFE to produce perhalofluoropropanes and/or pentanes, wherein the total number of fluorines in said propanes and pentanes is equal to the sum of the fluorines in the methanes and fluoroolefins being reacted.

The process of the invention comprises producing perhalofluoropropanes and/or pentanes by:

(i) contacting (a) a dihalodifluoromethane, CXYF2, wherein X and Y are independently Cl or Br, with (b) at least one of tetrafluoroethylene and chlorotrifluoroethylene while in the presence of (c) a catalytic amount of an effective aluminum chlorofluoride, at a temperature and pressure effective to result in the formation of (d) at least one of a perhalofluoropropane having 5 to 6 fluorine atoms and 2 to 3 nonfluorohalogen atoms, e.g., bromine and/or chlorine atoms, and a perhalofluoropentane having 8 to 10 fluorine atoms and 2 to 4 nonfluorohalogen atoms, e.g., bromine and/or chlorine atoms; the total number of fluorine atoms in said propane and/or pentane products being the sum of the number of fluorine atoms in the dihalodifluoromethane and the number of fluorine atoms in the TFE and/or CTFE, and;

(ii) recovering at least one of said propanes and pentanes.

In one aspect of the invention, the dihalodifluoromethane comprises CCl2F2 (CFC-12), the fluoroethylene comprises TFE and the aluminum chlorofluoride contains about 3 to about 64% F by weight, normally about 16 to 61 % F by weight. Such aluminum chlorofluorides, which correspond to AlCl3-xFx, wherein x is typically about 1.0 to about 2.8, are hereinafter referred to as "modified aluminum chlorides". Modified aluminum chlorides are conveniently prepared by reacting commerically available anhydrous AlCl3 with one or more chlorofluorocarbons, hydrochlorofluorocarbons, or hydrofluorocarbons as disclosed in U.S. Pat. No. 5,157,171 to Sievert, et. al. at column 4 line 2 through column 5 line 4, the entire disclosure of which is hereby incorporated herein by reference.

In one embodiment of the invention, the reaction conditions, e.g., the mole ratios of reactants, their feed rates, and temperature and pressure, are controlled so as to favor a one-to-one reaction of the dihalodifluoromethane with the fluoroolefin, while in the presence of a modified aluminum chloride catalyst, and result in the formation of halofluoropropanes as the predominant products as illustrated by equation (1).

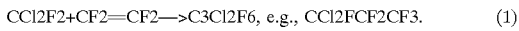
$$CCl2F2 + CF2=CF2 \rightarrow C3Cl2F6, \text{ e.g., } CCl2FCF2CF3. \quad (1)$$

In another embodiment, the reaction conditions are adjusted for promoting production of halofluoropentanes as the predominant products via a one-to-two reaction stoichiometry, while in the presence of a modified aluminum chloride catalyst, as illustrated in equation (2).

$$CCl2F2 + 2\ CF2=CF2 \rightarrow C5Cl2F10, \text{ e.g., } C2F5CCl2C2F5. \quad (2)$$

In still another aspect of the invention, the reaction products, as perhalofluoropropanes and/or as perhalofluoropentanes are treated with one or more reducing means under conditions effective for converting the non-fluorohalide groups of the propanes and pentanes, i.e., the —CXY— groups, wherein X and Y are independently Cl or Br, to —CHX— or —CH2— groups, usually the latter. The reducing means include photochemical reducing means, chemical reducing means, catalytic hydrogenation reducing means, among other suitable means.

DETAILED DESCRIPTION

In accordance with the present invention one or more perhalofluoropropanes comprising (A) C3XYF6, when produced from TFE, (B) C3ClXYF5, when produced from CTFE, and perhalofluoropentanes having the formula C5XYF10, when produced from TFE, (C) C5Cl2XYF8, when derived from a mixture of TFE and CTFE; wherein X and Y stand for Cl or Br as defined above, can be prepared by reacting CXYF2, e.g., CCl2F2, with TFE and/or CTFE in the presence of a modified aluminum chloride catalyst. The reactions may be represented by equations (1) and (2) above, illustrated with CCl2F2 and TFE as the reactants.

The CXYF2 starting materials for the process of this invention can be selected from at least one member selected from the group of CCl2F2, CBrClF2, and CBr2F2. The fluoroolefin starting materials for the process of this invention are selected from one or more of CTFE (CClF=CF2) and TFE (CF2=CF2). The combination of these CXYF2 starting materials with these fluoroolefin starting materials in the presence of a modified aluminum chloride catalyst permits making reaction products selected from one or more of C3Cl4F4 isomers including CCl3CF2CClF2 and CCl3CClFCF3; C3BrCl3F4 isomers including CCl2FCF2CBrClF; C3Br4F4 isomers including CBr3CF2CBrF2; C3Cl3F5 isomers including CClF2CCl2CF3, CClF2CClFCClF2, CCl2FCClFCF3, CCl2FCF2CClF2, and CCl3CF2CF3; C3BrCl2F5 isomers including CF3CBrClCClF2, CClF2CF2CBrClF, CClF2CClFCBrF2, CBrCl2CF2CF3 and CBrF2CF2CCl2F; C3Br2ClF5 isomers including CBr2ClCF2CF3; C3Br3F5 isomers including CBr3CF2CF3 and CBrF2CBr2CF3; C3Cl2F6 isomers, including CCl2FCF2CF3 and CClF2CF2CClF2; C3BrClF6 isomers, including CBrClFCF2CF3, CBrF2CF2CClF2, and CF3CBrClCF3; C3Br2F6 isomers, including CBr2FCF2CF3, CBrF2CF2CBrF2, and CF3CBr2CF3; C5Cl4F8 isomers, including CF3CClFCCl2CClFCF3, CClF2CClFCF2CCl2CF3, and CClF2CF2CCl2CF2CClF2; C5BrCl3F8 isomers; C5Br2Cl2F8 isomers; C5Cl3F9 isomers including CClF2CF2CCl2CF2CF3, C5BrCl2F9 isomers; C5Br2ClF9 isomers; C5Br3F9 isomers including CBrF2CF2CBr2CF2CF3; C5Cl2F10 isomers including C2F5CCl2C2F5 and CF3CCl2CF2CF2CF3; C5BrClF10 isomers including C2F5CBrClC2F5 and CF3CBrClCF2CF2CF3; and C5Br2F10 isomers including C2F5CBr2C2F5 and CF3CBr2CF2CF2CF3.

Novel perhalofluoropropanes and pentanes that can be produced by using the inventive process comprise at least one member from the group of CClF2CF2CBrClF, CBrCl2CF2CF3 and CBrF2CF2CCl2F; CBr3CF2CF3 and CBrF2CBr2CF3; CClF2CClFCF2CCl2CF3 and CClF2CF2CCl2CF2CClF2; C5Br2Cl2F8 isomers; CClF2CF2CCl2CF2CF3, C5BrCl2F9 isomers; C5Br2ClF9 isomers; CBrF2CF2CBr2CF2CF3; C2F5CCl2C2F5 and CF3CCl2CF2CF2CF3; C2F5CBrClC2F5 and CF3CBrClCF2CF2CF3; C2F5CBr2C2F5 and CF3CBr2CF2CF2CF3. Such novel perhalofluoroalkanes can be used for making useful hydrofluorocarbons (HFCs) such as hydrofluoropropanes and hydrofluoropentanes. Such HFCs can be used as refrigerants, blowing agents, cleaning compositions, among other applications.

The process of equation (1) indicates a stoichiometry of one mole of CXYF2 per mole of TFE (or CTFE); however, an excess of either reactant may be used as desired with excess of the fluoroolefin promoting formation of the C5 product. Even at mole ratios of about 1:1 however, significant quantities of C5-product can be produced (equation (2)) along with C3-product (equation (1)). The relative proportions of the two reactants can be varied widely for producing a desired product or product mixture of products.

Generally, the mole ratio may vary from about 3 to 1 moles of CXYF2 component per mole of the fluoroolefin, to promote C3 production and from about 3 to 1.5 moles of the fluoroolefin per mole of the CXYF2 to promote C5 production.

In some cases, CCl2F2 may also be employed in the formation of modified aluminum chloride, as defined above, use of sufficient excess enables the production of modified aluminum chloride in situ from anhydrous aluminum chloride so that the catalyst modification reaction need not be carried out as a separate step. The ability to form the modified catalyst in situ constitutes an improvement over the art because the process can be practice by using AlCl3 thereby obviating a modified catalyst formation step. It is, however, important that the excess quantity, for example, of CCl2F2, avoids converting the AlClx-3Fx to AlF3 which in turn can adversely effect the inventive process. In some cases, the CCl2F2 and TFE and/or CTFE can be simultaneously contacted with the AlCl3.

The process can be conducted batchwise or in a continuous manner. In the continuous mode, a mixture of dihalodifluoromethane and fluoroolefin is passed through or over a bed or body of modified aluminum chloride which may be under agitation at suitable temperature and pressure to form a product stream, and the desired products are recovered from the stream by conventional methods such as fractional distillation. In some cases, the reactants can be added individually or simulataneously.

In the batch process, the reactants and catalyst may be combined in a suitable commercially available reactor to form a reaction mixture and the mixture held at a suitable temperature and pressure, normally under agitation, until a desired degree of conversion to the desired propanes and/or pentanes is attained. In one embodiment, the reactor is initially charged with the catalyst, and optionally with a diluent, then the dihalodifluoromethane and the fluoroolefin, as separate streams or as a combined stream, in a desired mole ratio, are fed into the reactor at a controlled rate and maintained therein until the reaction is substantially complete. If the reactor is fed with dihalodifluoromethane and catalyst in the substantial absence of fluoroolefin, then the system (reactor and ingredients) should be kept relatively cold, e.g., between about −78C and 10C, to minimize disproportionation of the dihalodifluoromethane to higher and lower fluorine content methanes.

The process may be practiced with or without a solvent or reaction diluent. Such material, if used, must be substantially inert to the reactants and catalyst, and also should boil at a temperature enabling separation from the propane and pentane reaction products. Representative of such solvents comprise at least one member from the group of CCl4, CF3CHCl2, CCl3CF3, propane and pentane products of the present invention process, e.g., CF3CF2CCl2F, CClF2CF2CClF2, CF3CF2CCl2CF2CF3, CF3CCl2CF2CF2CF3, and isomers, among others.

The reaction temperature may be varied, and normally is in the range of from about 0C to about 150C, usually in the range of from about 20C to about 110C.

The reaction pressure likewise may vary widely from subatmospheric to superatmospheric; but normally the reaction is carried out at elevated pressures, particularly at pressures generated autogenously in conformity with the reaction temperature employed. The pressure may be controlled by adjusting the amount of unreacted dihalodifluoromethane and fluoroolefin.

The reaction time, or time necessary for sufficient substantially complete reaction, can vary with the temperature chosen for the reaction. In general the higher the temperature the shorter the reaction time. The degree of reaction, however, is easily determined by the change in the autogenous pressure in the reaction vessel, because the pressure drops as the reaction proceeds, so that the time at which the pressure stops decreasing can be taken as the end of the reaction period. The reaction time can also vary with the quantity or volume of reactants in the reactor. Generally, the reaction time, is in the range of from about 0.25 h to about 8.0 hours are normally employed temperature ranges.

The amount of modified aluminum chloride generally employed is in the range of from about 1 to 20 percent based on the weight of the dihalodifluoromethane reactant.

The reaction products may be recovered from the reactor by using any suitable conventional means such as by filtration or distillation. It is usually convenient to decompose the catalyst by treatment with water and then recover the product by distillation.

If desired, the perhaloproducts of the invention process may be hydrodehalogenated to hydro-derivatives comprising at least one hydrogen substituent and correspondingly one less nonfluorohalogen substitutent than present in the starting perhalofluorocarbon by being treated with one or more reducing means. Examples of suitable reducing means comprise at least one of photochemical, chemical, and normally catalytic hydrogenation means. Catalytic hydrogenation may generally be effected with molecular hydrogen over a suitable catalyst, typically a Group VIII metal, as disclosed, for example, in Smith, U.S. Pat. No. 2,942,036 and Rao, U.S. Pat. No. 5,136,113; the entire disclosures of which are incorporated herein by reference.

Catalytic hydrogenation can be practiced in the liquid or vapor phase. Normally, the vapor phase is employed with a catalytic metal such as palladium that can be supported on carbon or alumina; usually the latter. Catalytic hydrogenation may generally be effected with molecular hydrogen over a suitable catalyst, typically a Group VIII metal, as disclosed, for example, in Smith, U.S. Pat. No. 2,942,036 and Rao, U.S. Pat. No. 5,136,113 which disclosures are incorporated herein by reference.

Hydrogenation can also be conducted in the vapor phase with a catalytic metal such as nickel, palladium, platinum, rhodium, iridium, among others. The catalytic metal is normally supported on a suitable carrier such as carbon or alumina. The use of alumina as a support for palladium is particularly desirable for hydrodechlorination and hydrodebromination as illustrated in Example 22 for the conversion of CF3CF2CCl2CF2CF3 to CF3CF2CH2CF2CF3. The use of carbon as a support for palladium is effective for hydrogenating, when a combination of hydrodehalogenation, dehydrofluorination, and hydrogen addition is desired as illustrated in Examples 20 and 21 for the conversion of CF3CF2CCl2CF2CF3 to CF3CHFCH2CF2CF3.

The hydrodehalogenation reactions of the present invention may be conducted at temperatures between about 25C and 250C, normally between about 50C and 200C, and typically between about 100C and 200C. The choice of optimum hydrodehalogenation temperature will be dictated by whether the halogen being removed or replaced is chlorine or bromine, the desired degree of conversion of the perhalofluoroalkane starting material, the percent loading of the active metal upon the support, among other factors. Perbromofluoroalkanes are more readily hydrodehalogenated than are perchlorofluoroalkanes.

The hydrodehalogenation reactions may be operated at pressures between atmospheric and 100 psig or higher. The choice of pressure may be dictated by the vapor pressure of the reactants, intermediates, and products.

The ratio of hydrogen to perhalofluoroalkane employed in the dehydrohalogenation reaction may vary from about 0.5 to about 10 on a molar basis, and usually should be from about 1 to 4. Relatively large excesses of hydrogen can be employed. A deficiency of hydrogen may be used to control the conversion rate of the perhalofluoroalkane if desired.

The products of the hydrodehalogenation reaction may be separated from excess hydrogen, if any, and HF, HCl, and/or HBr by-products by normal distillation or neutralization techniques. The products of the hydrodehalogenation comprise at least one member from the group of hydrofluoroalkanes, hydrofluoroalkenes, hydrohalofluoroalkanes, and hydrohalofluoroalkenes. Examples of hydrodehalogenation products from the hydrodechlorination of CF3CF2CCl2CF2CF3 (see Examples 20, 21, and 22) comprise at least one of CF3CF2CH2CF2CF3, CF3CHFCH2CF2CF3, CF3CF=CHCF2CF3, CF3CF2CHClCF2CF3, CF3CF=CClCF2CF3, among others.

The hydrohalofluoroalkanes, hydrofluoroalkenes, and hydrohalofluoroalkenes are intermediates in the formation of the hydrofluoroalkanes and may be separated from the hydrofluoroalkanes for conversion to the saturated products.

Hydrofluoropropanes and hydrofluoropentanes produced by hydrodehalogenation of the perhalofluoroalkanes comprise at least one of C3H4F4 isomers including CH3CF2CHF2, CH3CHFCF3, and CH2FCF2CH2F; C3H3F5 isomers including CHF2CH2CF3, CHF2CHFCHF2, CH2FCHFCF3, CH2FCF2CHF2, and CH3CF2CF3; C3H2F6 isomers including CH2FCF2CF3, CHF2CF2CHF2, and CF3CH2CF3; C5H8F4 isomers including CHF2CH2CH2CH2CHF2; C5H7F5 isomers including CHF2CH2CH2CH2CF3, and CHF2CHFCH2CH2CHF2; C5H6F6 isomers including CF3CH2CH2CH2CF3, CHF2CH2CHFCH2CF3, CHF2CHFCH2CH2CF3, and CHF2CF2CH2CH2CHF2; C5H5F7 isomers including CF3CH2CH2CHFCF3, CHF2CHFCHFCH2CF3, CHF2CF2CH2CHFCHF2, CHF2CF2CH2CH2CF3, and CHF2CH2CH2CF2CF3; C5H4F8 isomers including CF3CHFCH2CHFCF3, CHF2CHFCF2CH2CF3, CHF2CF2CH2CF2CHF2, CHF2CF2CH2CHFCF3, CF3CH2CH2CF2CF3, and CHF2CHFCH2CF2CF3; C5H3F9 isomers including CF3CHFCH2CF2CF3, CF3CH2CHFCF2CF3, and CHF2CF2CH2CF2CF3, C5H2F10 isomers including C2F5CH2C2F5 and CF3CH2CF2CF2CF3.

Novel hydrofluoroalkanes comprise at least one member from the group consisting of CHF2CH2CH2CH2CHF2; CHF2CH2CH2CH2CF3 and CHF2CHFCH2CHF2; CHF2CH2CHFCH2CF3, CHF2CHFCH2CH2CF3, and CHF2CF2CH2CH2CHF2; CF3CH2CH2CHFCF3, CHF2CHFCHFCH2CF3, CHF2CF2CH2CHFCHF2, CHF2CF2CH2CH2CF3, and CHF2CH2CH2CF2CF3; CF3CHFCH2CHFCF3, CHF2CHFCF2CH2CF3, CHF2CF2CH2CF2CHF2, CHF2CF2CH2CHFCF3, and CHF2CHFCH2CF2CF3; CHF2CF2C2CF2CF3. All of the above hydrofluoroalkanes can be used in the manner described above in connection with HFCs such as refrigerants, blowing and cleaning agents, among other applications.

In addition to hydrogenation, suitable chemical reducing means that may be used include reducting with zinc in the presence of an alcohol as disclosed, for example, by Morikawa, et. al., in International Patent Application 90/08753, and by Krespan in U.S. Pat. No. 4,935,558; reduction with a complex metal hydrides as disclosed by Clayton in European Patent Application Publication No. 0 508,631; reduction with hydrogen iodide or with H2 in the presence of iodine or hydrogen iodide as disclosed by Anton in U.S. Pat. No. 5,208,396; the entire disclosure of which are hereby incorporated herein by reference.

Suitable photochemical reducing means include reaction of the perhalocompound with alcohols in the presence of ultraviolet light as disclosed by Posta, et. al., in Czechoslovak Patent No. 136,735.

The various aspects of this invention may are more readily understood by reviewing the following examples that are provided to illustrate not limit the scope of the appended claims.

Examples 1 to 7 illustrate reacting CCl2F2 (CFC-12) with CF2=CF2 (TFE) catalyzed by separately prepared modified aluminum chloride catalyst while Example 8 utilizes initially unmodified AlCl3 as the catalyst.

Examples 8 to 16 utilize CBrClF2 and CBr2F2 as the dihalodifluoromethane reactant, with Example 16 showing the effect of using initially unmodified AlCl3 as the catalyst.

Examples 17 to 19 illustrate the use of CClF=CF2 (CTFE) in place of TFE.

Examples 20–22 illustrate preparing hydrofluorocarbons from perhalofluoropropanes and pentanes utilizing catalytic hydrogenation.

Analyses of reaction products, generally mixtures, were carried out using standard GC/GC-MS and 19F NMR methods, the abbreviations GC, GC-MS, and NMR standing for gas chromatography, gas chromatography-mass spectrometry, and nuclear magnetic resonance spectroscopy. Results are presented in GC area percents unless otherwise indicated with amounts less than about 1% generally omitted.

EXAMPLE 1

Reaction of CFC-12 with Tetrafluoroethylene

A 400 mL "Hastelloy" C shaker tube was charged with CCl3F-modified aluminum chloride (3.0 g). The tube was sealed, cooled to −78C, evacuated, and purged with nitrogen three times.

The reactor was then charged with CCl2F2 (50 g, 0.41 mole). The cold reactor was placed in the barricaded enclosure, and charged with 25 g (0.25 mole) of TFE. The reactor was warmed to 60C over the course of 0.25 h; during this time the pressure rose to 80 psig. The temperature was held at 60C for 1.3 h (pressure =80–85 psig) and then raised to 80C and held for 1 h (pressure=112–116 psig). The following day the reactor was discharged to afford 54.7 g of a clear supernatant over a brown solid. Analysis of the product by GC/GC-MS and 19F NMR indicated the following composition:

| Component | GC Area % | Mole % |
| --- | --- | --- |
| CCl2F2 | 1.3 | — |
| CCl2FCF2CF3 | 68.5 | 53.5 |
| CClF2CF2CClF2 | * | 13.9 |
| CCl3F | 0.1 | — |
| C2F5CCl2C2F5 | 26.5 | 29.8 |
| CCl3CF2CF3 | 2.1 | 2.8 |
| CCl2FCF2CClF2 | 0.2 | — |
| CCl4 | 0.8 | — |

C3Cl2F6 isomers were not separated by GC.

Noteworthy are the substantial yields of the hexafluorides, CCl2FCF2CF3 and CClF2CF2CClF2, and the decafluoride, CF3CF2CCl2CF2CF3. Also, the appearance of CCl3F and CCl4 along with the pentafluorides, CCl3CF2CF3 and CCl2FCF2CClF2, probably derived therefrom, indicates some disproportionation of the starting CFC-12 reactant had occurred.

The modified aluminum chloride catalyst of Example 1 was prepared as follows:

A 500 mL three neck round bottom flask containg a PTFE-coated stirring bar was charged with 50 g of aluminum chloride (AlCl3) in a dry box. The flask was passed out of the dry box and fitted with an addition funnel and a dry ice condenser connected to a nitrogen bubbler. The addition funnel was charged with 175 mL of CCl3F and the condenser was filled with a methanol/dry ice mixture. The CCl3F was gradually added to the flask and the mixture began to reflux vigorously. The reaction continued to reflux for a hour after all of the CCl3F had been added. The reaction was not heated. GC analysis of the supernatant liquid indicated it was essentially pure CCl4. The mixture was stirred overnight at ambient temperature and then volatiles were removed in vacuum. The resulting solid was dried under dynamic vacuum to afford 22 g of off-white powder. Analysis: weight % F=57.8; this corresponds to a composition that is approximately AlCl3F2.7.

EXAMPLE 2

Reaction of CFC-12 with Tetrafluoroethylene

A 400 mL "Hastelloy" C shaker tube was charged with CCl3F-modified aluminum chloride (1.5 g). The reactor was sealed, cooled to −78C, evacuated, and purged with nitrogen three times. The reactor was then charged with CCl2F2 (40 g, 0.33 mole). The cold reactor was placed in the barricade and charged with 15 g (0.15 mole) of TFE. The reactor was warmed to 30C over the course of 0.5 h and the pressure rose to 40 psig. TFE was then added to the reactor in 5 g increments at at temperature of 31–32C until a total of 50 g (0.50 mole) had been added; the pressure gradually rose to 114 psig. The reactor was then held at a temperature 31–2C for 3 h; the final pressure was 59 psig. The following day the reactor was discharged to afford 54.7 g of a clear supernatant over a brown solid. Analysis of the product by GC/GC-MS and 19F NMR indicated the following composition:

| Component | GC Area % |
|---|---|
| CClF2CF2ClF2/CCl2FCF2CF3 | 12.6 |
| CF3CCl2CF2CF2CF3 | .0 |
| CF3CF2CCl2CF2CF3 | 83.7 |
| C3Cl3F5 isomers | 1.0 |
| C5Cl3F9 isomers | 0.9 |

The modified aluminum chloride catalyst of Example 2 was prepared following a procedure similar to that described in Example 1 except that the reaction volatiles were removed promptly after the reaction ceased to reflux. Analysis: weight % F=47.7; weight % Al=26.6; this corresponds to a composition that is approximately AlClF2.

EXAMPLE 3

Reaction of CFC-12 with Tetrafluoroethylene

A 400 mL "Hastelloy" C shaker tube was charged with CCl3F-modified aluminum chloride (4 g) and 128 g of CCl3CF3 as a diluent. The reactor was sealed, cooled to −78C, evacuated, purged with nitrogen three times, and charged with CCl2F2 (50 g, 0.41 mole). The cold reactor was placed in the barricade and charged with 20 g (0.20 mole) of TFE. The reactor was warmed to 30C over the course of 0.25 h and the pressure rose to 45 psig. TFE was then added to the reactor in 5 g increments at a temperature of 29–30C over the next 1.5 h until a total of 50 g (0.50 mole) had been added; the pressure gradually rose to 42 psig. The reactor was then held at a temperature 30C for 3 h; the final pressure was 20 psig. The following day the reactor was discharged to afford 228.1 g of a clear supernatant over a dark solid. Analysis of the product by GC indicated the following composition:

| Component | GC Area % |
|---|---|
| CClF2CF2CClF2/CCl2FCF2CF3 | 18.3 |
| CCl3CF3 | 55.1 |
| CF3CCl2CF2C2CF3 | 0.3 |
| CF3CF2CCl2CF2CF3 | 21.2 |
| C3Cl3F5 isomers | 2.1 |
| CCl4 | 0.7 |
| C5Cl3F9 isomers | 0.8 |

The modified aluminum chloride catalyst of Example 3 was prepared as follows:

A 1 L four neck round bottom flask was charged with 150 g of aluminum chloride (AlCl3) in a dry box. The flask was passed out of the dry box and fitted with an addition funnel, a mechanical stirrer, a thermocouple, and a dry ice condenser connected to a nitrogen bubbler. The addition funnel was charged with 410 g of CCl3F and the condenser was filled with a methanol/dry ice mixture. The CCl3F was added to the flask over the course of about 1 h. After the addition was complete, the mixture was stirred for 1 h and then volatiles were removed in vacuum. The resulting solid was dried under dynamic vacuum with gentle warming (70C water bath) to afford 120.6 g of pale yellow powder. Analysis: weight % Al=25.5; this corresponds to a composition that is approximately AlCl1.3F1.7.

EXAMPLE 4

Reaction of CFC-12 with Tetrafluoroethylene

Example 3 was repeated with the exception that CHCl2CF3 was used as the diluent (120 g).

After charging with CCl2F2, the cold reactor was placed in the barricade and charged with 15 g (0.15 mole) of TFE. The reactor was warmed to 29C over the course of 0.25 h and the pressure rose to 65 psig. TFE was then added to the reactor in 5 g increments at at temperature of 27–33C over the next 1.3 h until a total of 50 g (0.50 mole) had been added; the pressure gradually rose to 105 psig. The reactor was then held at a temperature 30–38C for 3 h; the final pressure was 58 psig. The following day the reactor was discharged to afford 205.4 g of a clear supernatant over a dark solid. Analysis of the product by GC indicated the following composition:

| Component | GC Area % |
|---|---|
| CClF2CF2ClF2/CCl2FCF2CF3 | 20.6 |
| CHCl2CF3 | 59.3 |
| CF3CCl2CF2CF2CF3 | 0.2 |
| CF3CF2CCl2CF2CF3 | 16.8 |
| C3Cl3F5 isomers | 1.8 |
| C5Cl3F9 isomers | 0.7 |

EXAMPLE 5

Reaction of CFC-12 with Tetrafluoroethylene

A 400 mL "Hastelloy" C shaker tube was charged with aluminum chloride (2 g, 0.015 mole). The reactor was sealed, cooled to −78C, evacuated, purged with nitrogen three times, and charged with CCl2F2 (50 g, 0.41 mole). The cold reactor was placed in the barricade and charged with 25 g (0.25 mole) of TFE.

The reactor was warmed to 59C over the course of 0.3 h and the pressure rose to about 230 psig. The reactor was held at a temperature 52–60C for 3 h; the final pressure was 134 psig. The reactor was discharged to afford 41.1 g of a clear supernatant over a brown solid. Analysis of the product by GC/GC-MS indicated the following composition:

| Component | GC Area % |
|---|---|
| CClF2CF2ClF2/CCl2FCF2CF3 | 51.5 |
| CF3Cl2CF2CF2CF3 | 0.5 |
| CF3CF2Cl2CF2CF3 | 14.8 |
| CCl3C2F5 | 22.0 |
| CCl2FCF2CClF2 | 5.4 |
| CClF2CF2CCl2C2F5 | 3.1 |
| CCl2 = CCl2 | 0.8 |

The formation of CCl3C2F5 in such a substantial amount in the presence of initially unmodified AlCl3, the amount being significantly greater than that produced in the presence of initially modified aluminum chloride catalyst (Examples 14), indicates disproportionation of CCl2F2 had occurred to CCl3F (among other products) followed by addition of CCl3F to TFE. Further, it can be seen, in general, in comparison with the results of Examples 1–4, that the yields of the desired C3Cl2F6 and C5Cl2F10 products are lower than those obtained starting with an initially modified catalyst. The not insignificant yields of C3Cl2F6 and C5Cl2F10 products in Example 5 are believed the result of employing $CCl_2F_2$ in excess over the stoichiometric quantity.

EXAMPLE 6

Reaction of $CCl_2F_2$ with TFE—Continuous Process

A 1 L stainless steel, stirred autoclave was charged with 10 g of $AlCl_3-xF_x$ modified aluminum chloride. The autoclave was sealed and evacuated and 100 g of $CCl_3CF_3$ were drawn into the autoclave under vacuum. At a temperature of 13C and a pressure of 4 inches of vacuum, 20 g of TFE were fed to the autoclave. At an initial temperature and pressure of 10.9C and 32.3 psig, TFE and $CCl_2F_2$ were then co-fed to the reactor at rates of 50 g/h and 37.5 g/h, respectively as the reactor temperature was brought to 30–31C. Gas feeds was continued until the pressure reached 150 psig (31C); 2.98 moles of TFE had been fed and 2.00 moles of $CCl_2F_2$ had been fed. After stirring for 3.5 h, the reaction was shut down and 502 g of product were discharged. GC analysis of the product indicated the following major products:

| Component | GC Area % |
| --- | --- |
| $CClF_2CF_2CClF_2/CCl_2FCF_2CF_3$ | 22.6 |
| $CF_3CCl_2C_2F_5$ | 1.8 |
| $CCl_3CF_3$ | 15.5 |
| $CF_3CCl_2CF_2CF_2CF_3$ | 0.5 |
| $CF_3CF_2CCl_2CF_2CF_3$ | 52.0 |
| $CCl_3C_2F_5$ | 1.9 |
| $CClF_2CF_2CCl_2F$ | 0.1 |
| $CCl_4$ | 2.4 |
| $C_5Cl_3F_9$ isomers | 1.3 |

The modified aluminum chloride catalyst used in this Example was prepared following a procedure similar to that described in Example 3. Analysis: weight % Al=26.8; this corresponds to a composition that is approximately $AlCl_1F_2$.

EXAMPLE 7

Reaction of $CCl_2F_2$ with TFE—Continuous Process

A 1 L stainless steel, stirred autoclave was charged with 10 g of $AlCl_3-xF_x$. The autoclave was sealed and evacuated and 100 g of $CCl_3CF_3$ were drawn into the autoclave under vacuum. At a temperature of 16C and a pressure of 2 inch of vacuum, TFE and $CCl_2F_2$ were co-fed to the autoclave at rates of 80 g/h and 97 g/h, respectively as the reactor temperature was brought to 31–34C. Gas feeds were continued until the pressure reached 149 psig (31C); 3.29 moles of TFE had been fed and 3.90 moles of $CCl_2F_2$ had been fed. After stirring for 2 h, the reaction was shut down and 551 g of product were discharged. GC analysis of the product indicated the following major products:

| Components | GC Area % |
| --- | --- |
| $CClF_2CF_2CClF_2/CCl_2FCF_2CF_3$ | 30.2 |
| $CF_3CCl_2C_2F_5$ | 0.3 |
| $CCl_3CF_3$ | 14.0 |
| $CF_3CCl_2CF_2CF_2CF_3$ | 0.6 |
| $CF_3CF_2CCl_2CF_2CF_3$ | 41.5 |
| $CCl_3C_2F_5$ | 7.7 |
| $CClF_2CF_2CCl_2F$ | 0.8 |
| $CCl_4$ | 0.7 |
| $C_5Cl_3F_9$ isomers | 2.9 |

The modified aluminum chloride catalyst used in this Example was prepared following a procedure similar to that described in Example 3. Analysis: weight % Al=27.1; this corresponds to a composition that is approximately $AlCl_1F_2$.

EXAMPLE 8

Reaction of $CBrClF_2$ with Tetrafluoroethylene

A 400 mL "Hastelloy" C shaker tube was charged with $CCl_3F$-modified aluminum chloride (6.7 g). The tube was sealed, cooled to −78C, evacuated, and purged with nitrogen three times. The reactor was then charged with $CBrClF_2$ (89.8 g, 0.54 mole). The cold reactor was placed in the barricade and charged with 42 g (0.42 mole) of TFE. The reactor was warmed to 40C over the course of 1 h during this period the pressure rose to 37 psig. The temperature was held at 40C for 1 h (pressure =38 psig) and then raised to 80C and held for 2 h; during this time the pressure increased from 82 psig to 100 psig. The reaction was shut down at this point. The following day the reactor was discharged to afford 123.9 g of a orange supernatant over a dark solid. Analysis of the product by GC/GC-MS and 19F NMR indicated the following composition:

| Component | GC Area % | Mole % |
| --- | --- | --- |
| $CCl_2F_2$ | 0.7 | 0.8 |
| $CBrClF_2$ | 2.9 | 3.2 |
| $CBrClFCF_2CF_3$ | 54.0 | 39.9 |
| $CBrF_2CF_2CClF_2$ | * | 19.1 |
| $CCl_3CF_2CF_3$ | 0.4 | 0.3 |
| $C_5BrClF_{10}$ | 0.4 | |
| $C_2F_5CBrClCF_2CF_3$ | 27.2 | 24.8 |
| $C_5Br_2ClF_9$ (2) | 0.8 | |
| $CBr_2ClCF_2CF_3$ | 9.6 | 11.9 |
| $C_3BrCl_2F_5$ | 1.6 | — |

*$C_3BrCl_2F_6$ isomers not separated by GC.

The modified aluminum chloride catalyst used in this Example was prepared following a procedure similar to that described in Example 1.

EXAMPLE 9

Reaction of $CBrClF_2$ with Tetrafluoroethylene

The procedure of Example 8 was repeated using 38 g of TFE (0.38 mole), 30 g of $CBrClF_2$ (0.18 mole), and 3 g of $CCl_3F$-modified aluminum chloride (see Example 1). The TFE was added portionwise at a maximum temperature of 36C (maximum pressure =100 psig). The reaction was held at 36–39C for 1 h and then heated to 79–81C and held at that temperature for 2 h (final pressure=118 psig). The crude product weighed 58.3 g. Analysis of the product by GC and GC-MS indicated the following composition:

| Component | GC Area % |
|---|---|
| CBrF2CF2CClF2 | 14.7 |
| C5BrClF10 | 1.7 |
| C2F5CBrClC2F5 | 75.3 |
| C2F5CBr2C2F5 | 0.1 |
| C3Br2ClF5 | 1.3 |
| C5BrCl2F9 | 0.1 |
| C5Br2ClF9 (3) | 0.9 |

EXAMPLES 10, 11, and 12

Reaction of CBr2F2 with TFE using a CCl3F-modified Aluminum Chloride Catalyst

A 400 mL "Hastelloy" C shaker tube was charged with CCl3F-modified aluminum chloride (4 g) and CBr2F2 (63 g, 0.30 mole). The tube was sealed, cooled to −78C, evacuated, and purged with nitrogen three times. The cold reactor was placed in the barricade and charged with 30 g (0.30 mole) of TFE. The reactor was warmed to 100C over the course of 1 h during this period the pressure rose to 50 psig. The temperature was held at 99–101C for 4 h (max. pressure=60 psig) and then heating and agitation were stopped. The following day the reactor was discharged to afford 91.6 g of a clear supernatant over a dark solid.

The reaction between CBr2F2 and TFE was repeated following the procedure above at at temperature of 60C (EXAMPLE 11) and at a temperature of 30C (EXAMPLE 12). The GC analyses of these runs are compared in the table below.

| | Reaction Products, GC Area % | | |
|---|---|---|---|
| Component | Ex. 10 | Ex. 11 | Ex. 12 |
| CBrF2CF2CBrF2 | 14.0 | 13.7 | 13.7 |
| CBr2FCF2CF3 | 19.5 | 3.2 | 29.3 |
| CBrCl2CF2CF3 | 0.2 | 0.2 | 0.3 |
| CF3CBr2CF2CF2CF3 | 6.2 | 8.5 | 0.8 |
| C2F5CBr2C2F5 | 34.4 | 57.4 | 39.7 |
| CBrF2CBr2CF3 | 19.0 | 6.3 | 2.2 |
| CBr3C2F5 | 0.4 | 0.06 | 8.0 |
| C5Br3F9 | 1.2 | 1.2 | 2.1 |

The modified aluminum chloride catalyst used in Examples 10 and 11 were prepared following a procedure similar to that described in Example 1. Analysis: weight % Al=27.7; this corresponds to a composition that is approximately AlCl10.8F2.2. The modified aluminum chloride catalyst used in Example 12 was the same as that described in Example 1.

EXAMPLES 13 and 14

Reaction of CBr2F2 with TFE using a CCl3F-modified Aluminum Chloride Catalyst

A 400 mL "Hastelloy" C shaker tube was charged with CCl3F-modified aluminum chloride (see Example 1; 1 g) and CBr2F2 (42 g, 0.20 mole). The reactor was sealed, cooled to −78C, evacuated, and purged with nitrogen three times. The cold reactor was placed in the barricade, agitation was begun, and 10 g (0.10 mole) of TFE were added. The reactor was warmed to 0C over the course of 19 minutes; during this time the pressure decreased from 37 psig at −27C to 22 psig at 0C. An additional 17 g of TFE was added in five portions over the course of 1.2 h during which time the pressure rose to 61 psig. An additional 6 g of TFE were added bring the total pressure to 92 psig (total of 0.33 mole TFE added) and the reactor held at 30C for 13 h (final pressure=98 psig). Discharge of the reactor afforded 61.1 g of a yellow supernatant over a brown solid.

The reaction of CBr2F2 with TFE was repeated (EXAMPLE 14) using 105 g (0.50 mole) of CBr2F2 and 40 g (0.40 mole) of TFE in the presence of 2 g of CCl3F-modified aluminum chloride (see Example 1) at 30C. The results of these two experiments are given in Table below.

| | Product Distribution for Reaction of TFE with 12B2 | | | |
|---|---|---|---|---|
| | Ex. 13 | | Ex. 14 | |
| Component | GC Area % | Mole % | GC Area % | Mole % |
| CBrF3 | 0.08 | — | 0.5 | 1.2 |
| CBr2F2 | 0.8 | — | 0.9 | 1.3 |
| CBrF2CF2CBrF2 | 12.8* | 20.3 | 46.8* | 24.0 |
| CBr2FCF2CF3 | 1.5 | — | * | 31.5 |
| CF3CBr2CF3 | * | 1.7 | * | 1.1 |
| CF3CBr2CF2C2F5 | 2.3 | 1.7 | 0.7 | — |
| C2F5CBr2C2F5 | 72.6 | 69.2 | 29.0 | 23.3 |
| CBrF2CBr2CF3 | 2.0 | 1.9 | 2.8 | 3.1 |
| CBr3C2F5 | 2.4 | 2.8 | 14.3 | 14.6 |
| C2F5CBr2CF2CBrF2 | 2.2 | 2.1 | 1.9 | — |
| CBrF2CF2CBr3 | — | — | 0.2 | — |

*GC trace did not separate C3Br2F6 isomers accurately.

EXAMPLE 15

Reaction of CBr2F2 with TFE

A 1 L stainless steel, stirred autoclave was charged with 10 g of CCl3F-modified aluminum chloride. The autoclave was sealed and evacuated and 500 g (2.38 moles) of chilled CBr2F2 were drawn into the autoclave under vacuum. TFE was fed to the autoclave at a rate of 2.2 g/min at an initial temperature and pressure of 23C and 1 psig, respectively; the temperature was brought to about 30C. TFE feed was continued until the pressure reached 151 psig (29C). At this point the feed rate was decreased to 1.1 g/min. TFE was fed intermittently to the reactor keeping the pressure at a maximum value of 150 psig. The reaction was shut down after 4.76 moles of TFE had been fed to the reactor. Discharge of the reactor afforded 868 g of product. GC analysis of the product indicated the following major products:

| Component | GC Area % |
|---|---|
| C5BrF9 isomers | 0.9 |
| CBrF2CF2CBrF2 | 13.5 |
| CBr2FC2F5 | 6.3 |
| CBrCl2C2F5 | 0.8 |
| CF3CBr2CF2C2F5 | 4.2 |
| CF3CF2CBr2CF2CF3 | 63.1 |
| C3Br2ClF5 isomer | 1.4 |
| CBrF2CF2CBr2F | 1.4 |
| CBr3C2F5 | 3.0 |
| C5Br3F9 isomers | 2.1 |

The modified aluminum catalyst used in this Example was prepared following a procedure similar to that described in Example 3. Analysis: weight % Al=23.6; this corresponds to a composition that is approximately $AlCl_2F_1$.

EXAMPLE 16

Reaction of CBr2F2 with TFE using AlCl3 Catalyst

A 400 mL "Hastelloy" C shaker tube was charged with AlCl3 (99.99%, 2 g, 0.015 mole) and sealed. The tube was cooled to −78C, evacuated, and purged with nitrogen three times. The cold reactor was then charged with CBr2F2 (63 g, 0.30 mole) and placed in the barricade. The reactor was agitated and then charged with 10 g (0.10 mole) of TFE. The reactor was warmed to 31C over the course of 40 minutes as the pressure rose to 94 psig. An additional 20 g of TFE were added in three portions over the next 1.5 h. The temperature was held at 27–32C; the pressure was held at about 100 psig for most of this period, but rose to 162 psig as the last few grams of TFE were added. The reactor was held at about 30C for an additional 6 h as the pressure dropped to 60 psig. The following day, the reactor was discharged to afford 74.2 g of a clear supernatant over a brown solid. Analysis of the product by GC and GC-MS indicated the following composition:

| Component | GC Area % | Mole % |
|---|---|---|
| CBrClF2 | 6.4 | 16.3 |
| CBrF2CF2CClF2 | 54.8 | 15.7 |
| CBrClFC2F5 | * | 41.5 |
| CF3CBrClCF3 | * | 1.4 |
| CCl3CF2CF3 | 1.7 | 1.6 |
| CCl2FCF2CClF2 | 0.4 | — |
| C5BrClF10 | 0.4 | — |
| C2F5CBrClC2F5 | 17.8 | 13.8 |
| CBrCl2C2F5 | 11.4 | 8.3 |
| CBrF2CF2CCl2F | — | 1.3 |
| C2F5CBr2C2F5 | 0.07 | — |
| CBr2ClC2F5 | 3.2 | — |

*C3BrClF6 isomers not well separated on the GC column employed.

EXAMPLE 17

Reaction of CFC-12 with CTFE

A 400 mL "Hastelloy" C shaker tube was charged with 2 g of CCl3F-modified aluminum chloride. The reactor was sealed, cooled in dry ice, evacuated and purged with nitrogen three times. The reactor was re-evacuated and charged with CFC-12 (50 g, 0.41 mole) and CTFE (35 g, 0.30 mole). The reactor was warmed to 30C and held at 30–39C for 8 h (max pressure, 160 psig at 38C; final pressure, 130 psig at 35C). The product (10.3 g) consisted of a small amount of yellow supernatant over a brown solid. Analysis of the product by GC, GC-MS, and 19F NMR indicated the following composition.

| Component | GC Area % | Mole % |
|---|---|---|
| cyclo-cis-1,2-C4Cl2F6 | 23.1 | 21.1 |
| cyclo-trans-1,2-C4Cl2F6 | 34.2 | 28.7 |
| CClF2CClFCClF2 | 1.1 | 4.0 |
| CCl2FCClFCF3 | 14.4 | 15.3 |
| CClF2CF2CCl2F | 7.4 | 11.0 |
| CCl3C2F5 | * | 0.4 |
| CClF2CCl2CF3 | * | 1.5 |
| C5Cl4F8 (3 isomers) | 18.0 | |
| CF3CClFCCl2CClFCF3 (2 diastereomers) | | 4.5 |
| CClF2CClFCF2CCl2CF3 | | 7.8 |
| CClF2CF2CCl2CF2CClF2 | | 4.2 |
| CCl3CF2CClF2 | 0.4 | 0.6 |
| CCl3CClFCF3 | 0.6 | 0.7 |

The modified aluminum chloride catalyst used in this Example was prepared following a procedure similar to that described in Example 1. Analysis: weight % Al=26.6; this corresponds to a composition that is approximately AlCl1F2.

EXAMPLE 18

Reaction of CBrClF2 with CTFE

A 400 mL "Hastelloy" C shaker tube as charged with CCl3F-modified aluminum chloride (6.7 g). The reactor was cooled to −78C, evacuated, and purged three times with nitrogen. CBrClF2 (41 g, 0.25 mole) and CTFE (23 g, 0.20 mole) were sequentially condensed into the reactor. The cold reactor was placed in the barricade and agitation was begun. The reactor was heated to 40C and held for 3 h (50 psig) and then heated to 80C and held for 6 h. During the latter stage of the reaction the pressure increased form 80 to 90 psig. The product was discharged to give 55 g of a red-brown supernatant over a light-colored solid. Analysis of the product by GC, GC-MS, and 19F NMR indicated the composition listed below.

| Component | GC Area % | Mole % |
|---|---|---|
| CF3CBrClCClF2 | 34.8 | 48.5 |
| CClF2CF2CBrClF | 15.0 | 23.3 |
| CClF2CClFCBrF2 | * | 10.4 |
| CCl2FCF2CBrClF | 13.1 | 17.7 |
| CBrClF2 | 3.3 | — |
| CBrF2CClF2 | 0.7 | — |
| CBr2F2 | 0.3 | — |
| C3Cl2F4 | 3.9 | — |
| CBrF2CBrClF | 0.5 | — |
| C5ClF7 (4) | 3.8 | — |
| C4BrCl4F7 | 0.3 | — |
| C3BrCl2F3 (2) | 1.1 | — |

The modified aluminum chloride catalyst of Example 18 was prepared as follows:

A 2 L four neck creased round bottom flask was fitted with an addition funnel, a mechanical stirrer, a thermocouple, and a glycol/water-cooled condenser connected to a nitrogen bubbler. The flask was charged with 200 g of aluminum chloride (AlCl3). CCl3F (700 mL) was added to the flask over the course of about 1 h; during this time the temperature rose to about 67C and gradually dropped to about SOC. After the addition was complete, the mixture was stirred for 1 h. The supernatant was poured off and remaining volatiles were removed under vacuum with gentle warming (70C water bath) to afford 131 g of pale yellow powder. Analysis: weight % Al=29.5; this corresponds to a composition that is approximately AlCl0.5F2.5.

EXAMPLE 19

Reaction of CBr2F2 with CTFE

A 400 mL "Hastelloy" C shaker tube was charged with CCl3F-modified aluminum chloride (see Example 1; 3 g)

and CBr2F2 (54 g, 0.26 mole). The tube was sealed, cooled to −78C, evacuated, purged with nitrogen three times, and then charged with 29 g (0.25 mole) of CTFE. The cold reactor was placed in the barricade and warmed to 30C with agitation; the pressure rose to about 35 psig and then dropped to zero. The temperature was held at 29–35C for 6 h. The following day the reactor was discharged to afford 60.7 g of a clear supernatant over a brown solid. Analysis of the product by GC and GC-MS indicated the following composition:

| Component | GC Area % |
|---|---|
| CClF=CF2 | 5.8 |
| CBrF2CClF2 | 1.7 |
| cyclo-C4Cl2F6 (2) | 11.7 |
| C2Br2ClF3 | 0.8 |
| C3Br2ClF5 | 27.7 |
| C3Br2ClF5 | 7.7 |
| C5BrCl2F7 | 1.3 |
| C5BrCl2F7 | 1.5 |
| C5BrCl2F7 | 1.4 |
| C5BrCl2F7 | 1.1 |
| C3Br2ClF3 | 0.9 |
| C5Br2Cl2F8 | 2.0 |
| C5Br2Cl2F8 | 13.2 |
| C5Br2Cl2F8 | 3.6 |
| C5Br2Cl2F8 | 17.6 |

EXAMPLE 20

Hydrogenation of CF3CF2CCl2CF2CF3 over Pd/C Catalyst

A 15 inch (38.1 cm)×3/8 inch (0.95 cm) "Hastelloy" nickel alloy tube was filled with 4.68 gm (about 13 mL)0.5% Pd/C ground to 4/10 mesh. The catalyst was activated by heating at 120C for 135 min under a hydrogen flow of 50 sccm, 8.3×10−7 m3/s). The temperature of the reaction was raised to 175C while decreasing the flow of H2 to 22 sccm (3.7×10−7 m3/s) and increasing the flow of CF3CF2CCl2CF2CF3 to 7.3 sccm (1.2×10−7 m3/s). The gaseous effluent was found to be 93% CF3CF2CH2CHFCF3, an over hydgrogenation product.

EXAMPLE 21

Hydrogenation of CF3CF2CCl2CF2CF3 over Pd/C Catalyst

The reactor described in Example 20 was filled with 2.00 gm (about 6.0 cc) of 0.5% Pd/C ground to 4/10 mesh. The catalyst was activated by heating at 150C for 52 min. under a hydrogen flow of 50 sccm, 8.3×10−7 m3/s). The temperature of the reaction was lowered to 100C while decreasing the flow of H2 to 3.8 sccm (6.3×10−8 m3/s) and increasing the flow of CF3CF2CCl2CF2CF3 to 2.0 sccm (3.3×10−8 m3/s). The gaseous effluent was found to be 57% CF3CF2CH2CHFCF3, 9.4% CF3CF2CHClCF2CF3, 16% CF3CF=CHCF2CF3, 4.8% CF3CF2CH2CF2CF3, 2.8% CF3CF=CClCF2CF3, 1.5% CF3CHFCHClCF2CF3, as well as other unidentified by-products.

EXAMPLE 22

Hydrogenation of CF3CF2CCl2CF2CF3 over Pd/Al2O3 Catalyst

The reactor described in Example 20 was filled with 3.48 gm (about 6.0 cc) of .5% Pd/Al2O3 (Calsicat 1/8" pellets #64A-057) ground to 4/10 mesh. The catalyst was activated by heating at 100C for 50 min. under a hydrogen flow of 50 sccm, 8.3×10−7 m3/s). The temperature of the reaction was raised to 150C while decreasing the flow of H2 to 20 sccm (3.3×10−7 m3/s) and increasing the flow of CF3CF2CCl2CF2CF3 to 10.0 sccm (1.7×10−7 m3/s). The gaseous effluent was found to be 61% CF3CF2CHClCF2CF3, which can recycled, 25% CF3CF2CH2CF2CF3, 3.1% CF3CF=CClCF2CF3, <1% CF3CHFCH2CF2CF3, While certain aspects of the invention have been described in particular detail a person in this art would recognize that other aspects and embodiments are encompassed by the appended claims.

The following is claimed:

1. A composition which comprises at least one member from the group consisting of $CClF_2CF_2CBrClF$, $CBrCl_2C_2F_5$, $CBrF_2CF_2CCl_2F$, $CBr_3C_2F_5$, $CBrF_2CBr_2CF_3$, $CClF_2CClFCF_2CCl_2CF_3$, $CClF_2CF_2CCl_2CF_2CClF_2$, $C_5Br_2Cl_2F_8$ isomers; $CClF_2CF_2CCl_2C_2F_5$, $C_5BrCl_2F_9$ isomers; $C_5Br_2ClF_9$ isomers; $CBrF_2CF_2CBr_2C_2F_5$; $C_2F_5CCl_2C_2F_5$, $CF_3CCl_2CF_2CF_2CF_3$, $C_2F_5CBrClC_2F_5$, $CF_3CBrClCF_2CF_2CF_3$; $C_2F_5CBr_2C_2F_5$ and $CF_3CBr_2CF_2CF_2CF_3$.

2. The composition of matter of claim 1 comprising C2F5CCl2C2F5.

3. The composition of claim 1 wherein the composition comprises at least one member from the group consisting of $CCl_2CF_2CBrClF$, $CBrCl_2C_2F_5$, $CBrF_2CF_2CCl_2F$, $CBr_3C_2F_5$, and $CBrF_2CBr_2CF_3$.

4. The composition of claim 1 wherein the composition comprises at least one member from the group consisting of $C_5Br_2Cl_2F_8$ isomers, $C_5BrCl_2F_9$ isomers, $C_5Br_2ClF_9$ isomers, $CBrF_2CF_2CBr_2CF_2CF_3$, $C_2F_5CBrClC_2F_5$, $CF_3CBrClCF_2CF_2CF_3$, $C_2F_5CBr_2C_2F_5$ and $CF_3CBr_2CF_2CF_2CF_3$.

5. A composition of matter comprising $CCl_2FCF_2CF_3$, $CClF_2CF_2CClF_2$ and at least one member selected from the group consisting of $C_2F_5CCl_2C_2F_5$, $CCl_3CF_2CF_3$, and $CCl_3CF_3$.

6. The composition of matter of claim 1 comprising CBr3CF2CF3.

7. The composition of matter of claim 1 comprising at least one of $C_2F_5CBrClCF_2CF_3$, and $C_2F_5CBrClC_2F_5$.

8. The composition of matter of claim 1 comprising C2F5CBr2C2F5.

* * * * *